US008860443B1

(12) United States Patent
Roberts

(10) Patent No.: US 8,860,443 B1
(45) Date of Patent: Oct. 14, 2014

(54) DEVICE TO MEASURE THE MOISTURE OF HAY IN A ROUND BALER

(75) Inventor: Jeffrey S. Roberts, Hudson, WI (US)

(73) Assignee: Harvest Tec, Inc., Hudson, WI (US)

( * ) Notice: Subject to any disclaimer, the term of this patent is extended or adjusted under 35 U.S.C. 154(b) by 1086 days.

(21) Appl. No.: 09/507,591

(22) Filed: Feb. 22, 2000

(51) Int. Cl.
*G01N 27/04* (2006.01)
*A01F 15/07* (2006.01)
*G01N 27/48* (2006.01)

(52) U.S. Cl.
CPC ............... *A01F 15/07* (2013.01); *G01N 27/48* (2013.01)
USPC .......................................... 324/694; 324/640

(58) Field of Classification Search
CPC ...... G01N 27/048; G01N 22/04; A01F 15/07; A01D 78/00
USPC ........................... 324/695, 696, 600, 640, 694
See application file for complete search history.

(56) References Cited

U.S. PATENT DOCUMENTS

| | | | | |
|---|---|---|---|---|
| 4,710,757 A | * | 12/1987 | Haase | 340/684 |
| 4,812,741 A | * | 3/1989 | Stowell | 324/695 |
| 5,570,030 A | * | 10/1996 | Wightman | 324/694 |
| 5,716,272 A | * | 2/1998 | Nelson | 460/7 |
| 5,845,529 A | * | 12/1998 | Moshe et al. | 324/640 |
| 6,329,923 B2 | * | 12/2001 | Hog | 340/601 |
| 6,377,058 B1 | * | 4/2002 | Pemrick | 324/695 |

* cited by examiner

*Primary Examiner* — Cynthia Britt
(74) *Attorney, Agent, or Firm* — Skinner and Associates; Joel Skinner

(57) ABSTRACT

The device that has been invented senses moisture contact of round bales as they are formed in the chamber of a round baler, by supplying voltage to a sensor located on one of the side walls of the baler and reading the voltage on a second sensor located on the opposing side wall of the baler.

3 Claims, 1 Drawing Sheet

DEVICE TO MEASURE THE MOISTURE OF HAY IN A ROUND BALER

SUMMARY OF THE INVENTION

The device that has been invented measures the moisture content of hay that is being baled by a round baler on a continuous basis. As hay passes between two sensing points, one each mounted on the outside vertical surfaces of the baler, electrical conductivity from one sensing point to the other is affected by the moisture content of the bale. Sensing across the entire width of the bale provides an improved reading of moisture content by sampling a larger area of the bale compared to conventional moisture sensor for round balers that are mounted only on one side of the baler and conduct electricity between two points from one side of the baler only.

BACKGROUND OF THE INVENTION

Hay, a major crop for feeding livestock, is cut in the field, dried by the natural elements to a moisture content below 18%, and then packaged in bales by implements that pick up the hay and form the bale. One type of hay baler that has become the most popular type of implement in the last twenty years is the round baler. This implement uses tines rotating on a shaft to pick up the hay from the field and deliver it to a chamber. In the chamber, the hay is rotated by moving belts, chains or rollers, so that it is wrapped in a tight cylinder of increasing size as hay is delivered to the chamber. At the time the chamber becomes full, the bale of hay is tied by a means built into the baler and then discharged.

To prevent spoilage due to mold growth, the hay must be harvested at moisture contents below 18%. Since an individual field of hay will vary in moisture from location to location and over time, an increasingly popular method for monitoring moisture in the bale, is to mount a moisture sensing device on one side of the baler and conveying a reading to the operator of the baler on a continuous basis as the hay is passing over this sensor. The devices in common use are sensors constructed of non-conductive material with two electrodes isolated from the baler frame and from each other. Electrical conductivity between the two electrodes in the sensor is a function of moisture content, as the hay conducts more electricity as the moisture content increases. Electrical conductivity, however is also affected by other factors such as pressure exerted against the sensor by the bale.

Since these conventional sensors are mounted on one side of then baler, they do not provide for a sample of the entire bale. If moisture on one side is not representative of the entire bale, the moisture reading coming from the conventional pad will be misleading. The sensing device that has been invented senses across the entire width of the bale and therefore provides improved moisture readings over the conventional sensor.

SPECIFICATIONS

Figure 1:
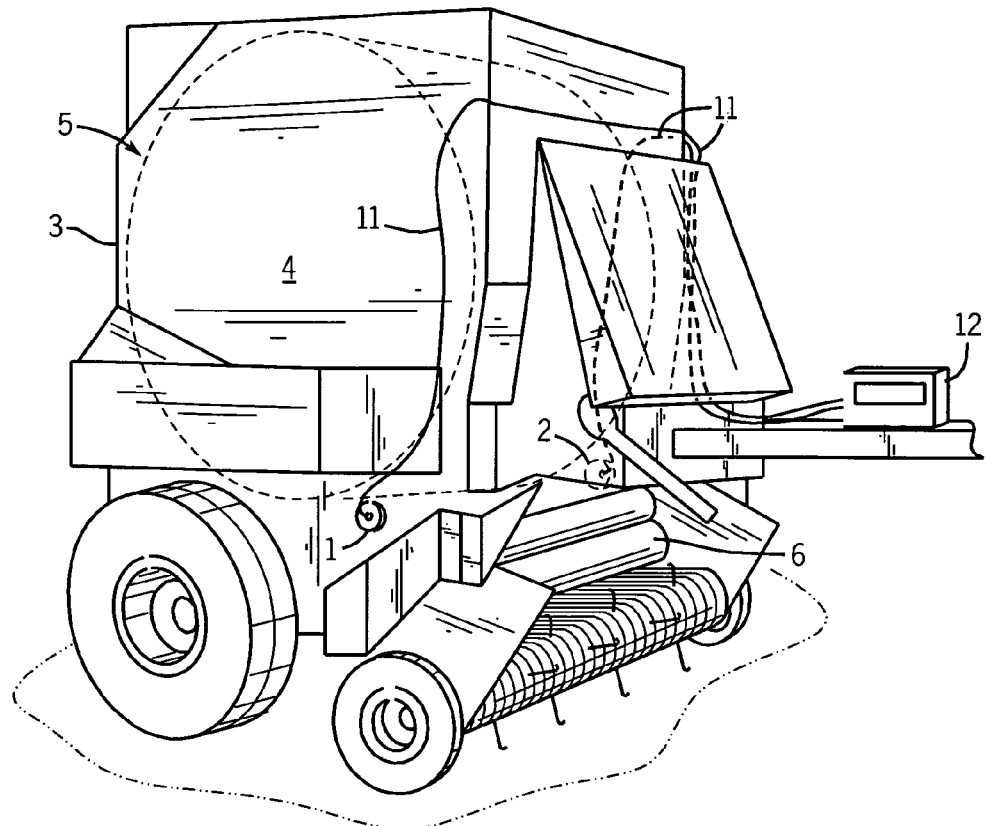
FIG. 1: View of a typical round baler with the positioning of the sensors.
Figure 2:
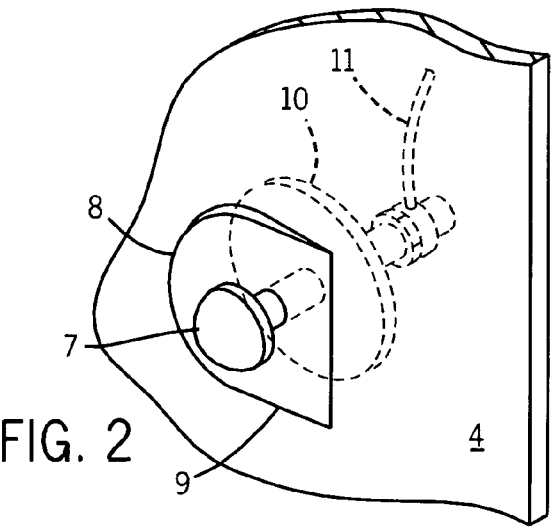
FIG. 2. Close-up view of a sensor with its critical parts.

Sensing devices FIGS. 1, 1 and 2 are designed to be mounted on the side wall of a round baler 3 so that part of the sensor is accessible outside the baler's side wall 4 and part of the sensor extends into the chamber of the baler where the bale 5 is formed. The preferable location for the sensors 1 and 2 is directly above the baler's starter or bottom roll 6. In this location, the hay entering the baler will come in contact with the sensor soon after entering the chamber. As the bale increases in size, newly introduced hay will come into contact with the sensor as the bale 5 rotates in the chamber. Each sensing device 1 and 2 has an electrode FIG. 2, 7 constructed of conductive material, preferably stainless steel. The electrodes 7 are extended inward slightly so that hay in the bale 5 contacts the electrodes as it rotates in the chamber. The electrodes 7 are mounted in the housings 8 of the sensors. These housings 8 must be constructed of a non conductive material so that the electrodes 7 are isolated from the frame of the baler 3. The front edge of the housings is tapered forward 9 so that the hay in the bale 5 will not catch on the sensor as it rotates in the bale chamber and the electrodes 7 will be in contact with the hay in the bale.

On the outside of the baler's side wall 4 the electrode is constructed in such a fashion so that it can be isolated from the side wall of the baler 4 by a non-conductive isolator 10. A conductors such as wires 11 will attach directly to each electrode. This connection must be outside of the baler's side wall 4 so that the bale 5 does not contact the conductors.

The conductors 11 are routed to a readout box 12. One of the conductors 11 is connected to a direct current power source between one and thirty volts. The opposite sensor picks up the voltage conducted through the hay bale 5. As the bale increases in moisture content, the conductivity of voltage between 1 and 2 increases. The voltage reading coming off of the non-powered sensor 1 or 2 is scaled to moisture and displayed in the readout box 12. An example of the scaling of moisture to voltage across the bale is as follows where the direct current power source supplied to sensors 1 or 2 is ten volts:

| voltage conducted between 1 and 2 | scaled moisture reading |
| --- | --- |
| 10 volts | above 40% |
| 9.96 volts | 38% |
| 9.54 volts | 36% |
| 9.00 volts | 34% |
| 8.00 volts | 32% |
| 6.95 volts | 30% |
| 5.98 volts | 28% |
| 5.05 volts | 26% |
| 4.32 volts | 24% |
| 3.92 volts | 22% |
| 3.60 volts | 20% |
| 3.39 volts | 18% |
| 3.12 volts | 16% |
| 2.96 volts | 14% |
| 2.80 volts | 12% |
| 2.71 volts | 10% |

As the voltage supplied to one sensor 1 or 2 is increased or decreased from the example above, different scaling can be used to display moisture in the readout box 12.

What is claimed:

1. A hay baler having the capability of measuring moisture, based on conductivity, in hay as it is being baled, comprising:
   a. a baler including a housing including a pair of opposing side walls separated a predetermined distance, and a bale forming chamber disposed between the side walls; and
   b. a hay moisture measurement system for measuring moisture in hay as the hay is being baled in the baler, the moisture measurement system including:
      i. a powered sensor disposed on one side wall of the baler, the powered sensor including a conductive electrode and a nonconductive housing connecting the electrode to the one side wall, the powered electrode being adapted to directly contact hay moving in the baler;

ii. a non-powered sensor disposed on the opposite side wall of the baler a predetermined distance from the powered sensor to permit conduction of direct current across moving hay, the non-powered sensor including a conductive electrode and a nonconductive housing connecting the electrode to the opposite side wall, the powered electrode being adapted to directly contact hay moving in the baler, and iii. a readout system including a voltage supply supplying between one and thirty volts of direct current to the powered sensor, a voltage reader, a display, and conductors communicatively connecting the sensors to the readout system, whereby electrical conductivity between the sensors across hay, contacting both the powered sensor and the non-powered sensor, moving in the bale forming chamber is a function of hay moisture content, whereby for a given voltage of direct current supplied to the powered sensor, an increasing voltage reading on the non-powered sensor represents increasing hay moisture content and a decreasing voltage reading on the non-powered sensor represents a decreasing hay moisture content.

2. A device as in claim 1 where the voltage supplied to one of the sensors is ten volts of direct current and the scaled readings of moisture are 40% for voltage readings between 10 and 9.74 volts, 38% for readings between 9.73 and 9.27 volts, 36% for readings between 9.26 and 8.50 volts, 34% for readings between 8.49 and 7.48 volts, 32% for readings between 7.47 and 6.46 volts, 30% for readings between 6.45 and 5.51 volts, 28% for readiness between 5.50 and 4.70 volts, 26% for readings between 4.69 and 4.12 volts, 24% for readings between 4.11 and 3.78 volts, 22% for readings between 3.77 and 3.50 volts, 20% for readings between 3.49 and 3.28 volts, 18% for readings between 3.27 and 3.04 volts, 16% for readings between 3.03 and 2.88 volts, 14% for readings between 2.87 and 2.76 volts and 12% for readings between 2.75 and 2.65 volts are read on the sensor opposite to the sensor to which the voltage is supplied.

3. The hay baler of claim 1, wherein housings of the sensors include a portion which extends into the bale forming chamber and has a front edge which tapers forward, and wherein a portion of each electrode extend through the extended portion, whereby moving hay contacts the sensor for conductivity and moisture measurement but will not catch on the sensor.

* * * * *